United States Patent [19]

Hosoya et al.

[11] 4,239,040
[45] Dec. 16, 1980

[54] CAPSULE FOR MEDICAL USE

[75] Inventors: Takeshi Hosoya; Fumihiro Tanaka; Kazuo Noguchi, all of Tokyo, Japan

[73] Assignee: Kabushiki Kaisha Daini Seikosha, Tokyo, Japan

[21] Appl. No.: 841,985

[22] Filed: Oct. 13, 1977

[30] Foreign Application Priority Data

Oct. 19, 1976 [JP] Japan ................................. 51-125234
Oct. 22, 1976 [JP] Japan ................................. 51-126909

[51] Int. Cl.³ .......................................... A61M 31/00
[52] U.S. Cl. ............................... 128/213 R; 128/260; 128/769
[58] Field of Search ................... 128/2 B, 2 PF, 2 R, 128/2 W, 213, 260

[56] References Cited

U.S. PATENT DOCUMENTS

| | | | |
|---|---|---|---|
| 3,057,344 | 10/1962 | Abella et al. | 128/2 F |
| 3,118,439 | 1/1964 | Perrenoud | 128/260 |
| 3,528,429 | 9/1970 | Beal et al. | 128/260 |
| 3,844,285 | 10/1974 | Laby | 128/260 |
| 4,077,405 | 3/1978 | Haerten et al. | 128/260 |

*Primary Examiner*—William E. Kamm
*Attorney, Agent, or Firm*—Robert E. Burns; Emmanuel J. Lobato; Bruce L. Adams

[57] ABSTRACT

A capsule for discharging drugs into a live body or collecting samples from the body comprises an external cylinder having slidably mounted therein an internal cylinder. The internal cylinder is retained by a meltable thread at one end of the external cylinder against the biasing force of a compression spring and upon melting of the thread, the spring effects sliding of the internal cylinder to the other end of the external cylinder and during this sliding movement, a drug is pushed out of the external cylinder ahead of the moving internal cylinder or a body sample is withdrawn into the external cylinder behind the moving internal cylinder. An electric circuit including a tunable receiver responds to an externally transmitted electric signal to energize a heater for melting the thread to thereby effect sliding movement of the internal cylinder at the desired time.

9 Claims, 11 Drawing Figures

CAPSULE FOR MEDICAL USE

BACKGROUND OF THE INVENTION

The present invention relates to a capsule for medical use and which is placed in a live body to collect a sample from the body or to release drugs into the body.

The collection of inside body fluid or the release of drugs by placing the capsule at a specified position in the body by means of swallowing down or the like process is a very effective means for medical treatment, but the capsule must be light in weight and small in size to be swallowed through the mouth; moreover, the necessary quantity of sample or dosing drugs should also be obtainable.

SUMMARY OF THE INVENTION

It is an object of this invention to provide a capsule for medical use to collect inside body fluid or to release drugs at a specified position in a live body.

According to this invention, the said capsule can be made miniature in size and light in weight so as to be easily swallowed, and moreover can collect sufficient quantity of the inside body fluid for examination or release sufficient quantity of drugs for medical treatment.

Other and further objects, features and advantages of the invention will become apparent from the following description of the preferred embodiments.

DESCRIPTION OF THE PREFERRED EMBODIMENTS

The preferred embodiments of this invention will be described in conjunction with FIGS. 1 to 11 and the following examples.

EXAMPLE 1

Figure 1:
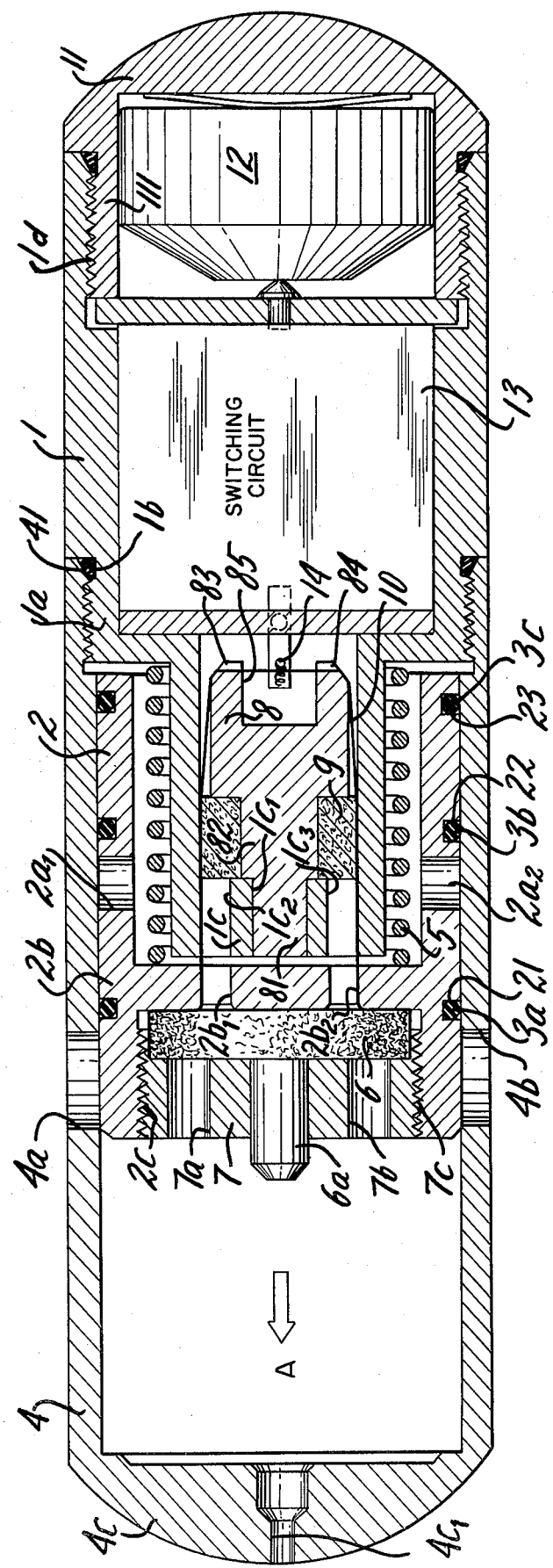
FIG. 1 is a cross-sectional view of one embodiment of capsule for medical use according to the invention.
Figure 2:
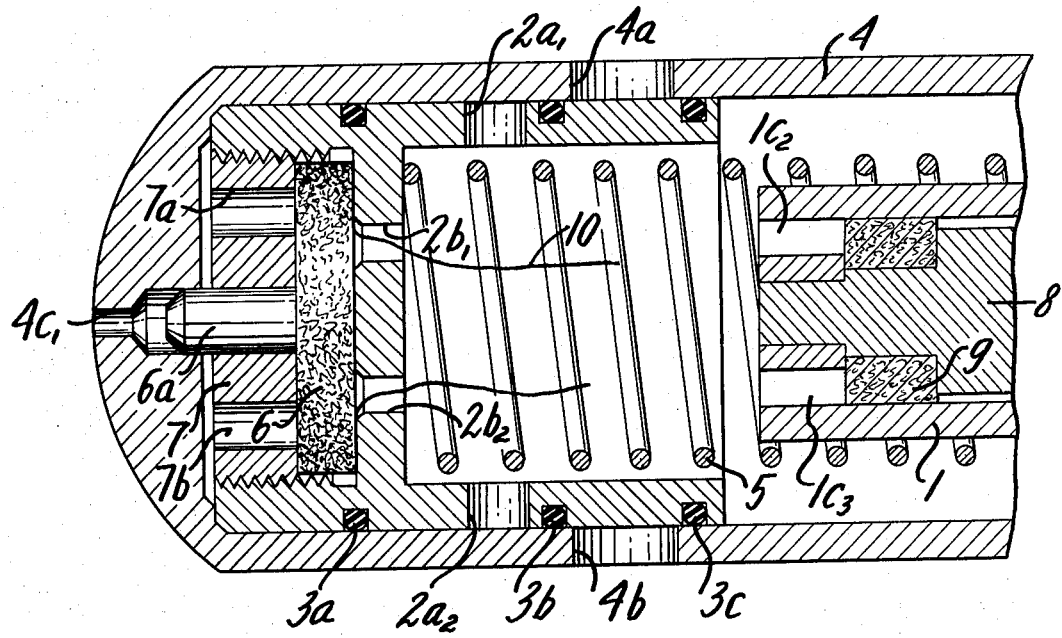
FIG. 2 is a fragmentary cross-sectional view of the capsule shown in FIG. 1 but showing the parts in a different operating state.

This example shows a capsule for medical use to collect samples and will be described with reference to FIGS. 1 and 2.

"1" is a cylindrical body frame having a stepped portion "1a" and an inlaid groove "1b" along the circumference thereof and further comprises of a supporting portion "1c" having inserting holes "1c1, 1c2 & 1c3" at the front end portion thereof and an inserting groove "1d" circumferentially at the rear end portion thereof. "2" is a recovery cylinder having liquid-sampling holes "2a1 & 2a2" opening at the external circumference thereof a supporting portion "2b" having inserting-holes "2b1 & 2b2" and a threaded portion "2c" for fixing a thread guard "7", described later, is located at the front end portion thereof along the internal circumference thereof. The recovery cylinder "2" is fitted slidably with the internal circumferential surface of an external cylinder "4" through sealing packing rings "3a, 3b & 3c". And on the external circumference of said recovery cylinder "2" are provided recessed grooves "21, 22 & 23" for receiving said sealing packing rings "3a, 3b & 3c" respectively. "4" is an external cylinder having collecting holes "4a & 4b" at the middle portion of the external circumference thereof, a cover portion "4c" having a damper hole "4c1" at the front portion thereof and a projected portion "41" on the rear internal circumference thereof for insertion into said inserting groove "1b" thereby shielding the front half portion of the body frame "1". A circular coil spring "5" is disposed between said supporting portion "2b" and said stepping portion "1a" and helps form an empty space for collecting the sample by biasing said recovering cylinder "2" in the direction of arrow mark A. A disc-shaped packing "6" having a pillar-shaped plug "6a" is inserted in the front recessed portion of said recovery cylinder "2" and this packing "6" is also fixed to the recovery cylinder "2" by the disc-shaped thread guard "7" having driving holes "7a & 7b" and a threaded portion "7c" at the external circumference thereof threaded into the threaded portion "2c" of the recovery cylinder "2". "8" is a cylindrical disc-shaped thread hanger press-fitted into said inserting hole "1c1" at the front end "81" thereof and has a stepped portion "82" at the external circumference thereof, cutting slits "83 & 84" to wedge a thread "10", described later, thereinto and a circular empty hole "85" at the rear end portion thereof. "9" is a circular disc-shaped packing to seal up the interior of said body frame "1" and is fixed to said stepped portion "82". "10" is a flexible thread to restrain the movement of said recovery cylinder "2" in the direction of arrow mark A by the compression force of said spring "5" and one end of said thread "10" is fixed by pressure between said supporting portion "2b" and said packng "6" and wedged into the cutting slits "83 & 84" through the inserting holes "2b1 & 1c2" and the other end of said thread "10" is likewise fixed the same therebetween through the inserting holes "1c3 & 2b2". "11" is a rear cover having a projected portion "111" to be inserted into said inserting groove "1d" of the internal circumference of said body frame "1" for shielding the rear end portion of said body frame "1" and the rear cover holds a power cell "12" for a switching circuit "13" and a heater "14" described later, therein. The said switching circuit "13" is mounted in the body frame "1" and controls the flow of current to said heater "14" by switching-on the heater only upon receipt of an externally transmitted instructing electric signal. The said heater "14" is connected to said switching circuit "13" and said power cell "12" and fixed so as to make contact with said thread "10".

Figure 3:
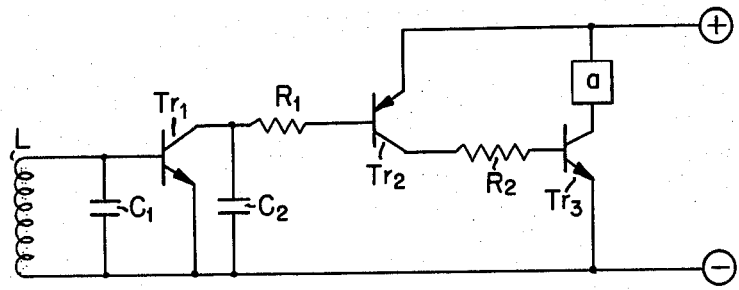
FIG. 3 is a schematic diagram of one embodiment of electric switching circuit for the capsule for medical use shown in FIG. 1.

One embodiment of this switching circuit "13" will be described in detail referring to FIG. 3.

"L" is a receiving coil, "$C_1$" is a tuning condenser, "$C_2$" is a detecting condenser, "$Tr_1$, $Tr_2$, & $Tr_3$" are transistors, "$R_1$ & $R_2$" are resistors and "a" is an electrically operated latch to release an operation arresting mechanism. Under the condition when no electric wave is transmitted from outside, form the voltage between the base and emitter of said transistor "$Tr_1$" is low and the "$Tr_1$" remains in cut-off condition, so that said transistors "$Tr_2$ & $Tr_3$" are also held in cut-off condition, accordingly no electric current flows in the circuit. However when a strong electric wave signal is transmitted sufficient to produce an AC electromotive force at both ends of said circuit corresponding to the frequency of said receiving tuner circuit composed of said receiving coil "L" and said tuning condenser "$C_1$" the collector and emitter of said transistor "$Tr_1$," repeat conductive and cut-off operations. But the condenser "$C_2$" is connected in parallel to the collector and emitter terminals of the transistor "$Tr_1$", and the time constant circuit composed of this condenser "$C_2$" and the resistor "$R_1$" has a sufficiently as compared with the tuning frequency, so that the electric charge stored in the condenser "$C_2$" during the cut-off condition of the transistor "$Tr_1$" is quickly forced to discharge during the conductive condition of said transistor "$Tr_1$", and therefore the base current of the transistor "$Tr_2$" flows continuously. By this base current, the collector and emitter of the transistor "$Tr_2$" become conductive therebetween, accordingly the base current of the transistor "$Tr_3$" flows through the resistor "$R_2$", therefore the transistor "$Tr_3$" becomes conductive and thereby the current flows to the latch actuator "a" which is necessary for actuating the capsule such as a heater, solenoid, etc. connected to the collector of the transistor "$Tr_3$" and the power source. Accordingly, if the external electromagnetic wave is applied continuously for some predetermined time sufficient to actuate said latch "a", the capsule can be operated thereby.

Hereafter, the operation of said capsule for medical use will be described.

This capsule is inserted in a live body by swallowing down or the like process and when it arrives at the specified place therein, the electronic signal is produced and the thread "10" is cut off by fusing with the heater "14" by means of actuating the switching circuit "13" according to current flow thereto from the power cell "12" and thereby the recovery cylinder "2" moves in the direction of arrow mark A by the biasing force of the spring "5". At this time, the fluid of the live body is inhaled in the recovery cylinder "2" when the collecting holes "4a & 4b" align with the collecting holes "2a1 & 2a2" as the internal pressure of the recovery cylinder "2" reduces. And at the same time, unnecessary gas, liquid or the like which existed in the empty space of the external cylinder "4" is released therefrom to the exterior through the damper hole "4c1". And then, the recovery cylinder "2" moves till the front end surface thereof comes into contact with the internal surface of the cover "4c" as shown in FIG. 2 and thereby the collecting holes "4a & 4b" are sealed by the packing rings "3b & 3c" and the collecting holes "2a1 & 2a2" are sealed by packing rings "3a & 3b". Furthermore, the pillar-shaped plug "6a" of the packing "6" enters into and seals up the damper hole "4c1" and prevents movement of the recovery cylinder "2" by external pressure.

As described above, as the capsule of this example 1 is composed of a receiving means using a supermicro electro-circuit, a releasing means using a supermicro heater, an arresting means including a flexible thread to restrain the recovery cylinder directly to the body frame and a collecting means constituted of an external cylinder having space to collect the sample and a spring to effect sliding movement of said external cylinder, the capsule can be made miniature in size and moreover, can be used to obtain sufficient quantity of inside body sample necessary for medical examination and analysis.

EXAMPLE 2

Figure 4:
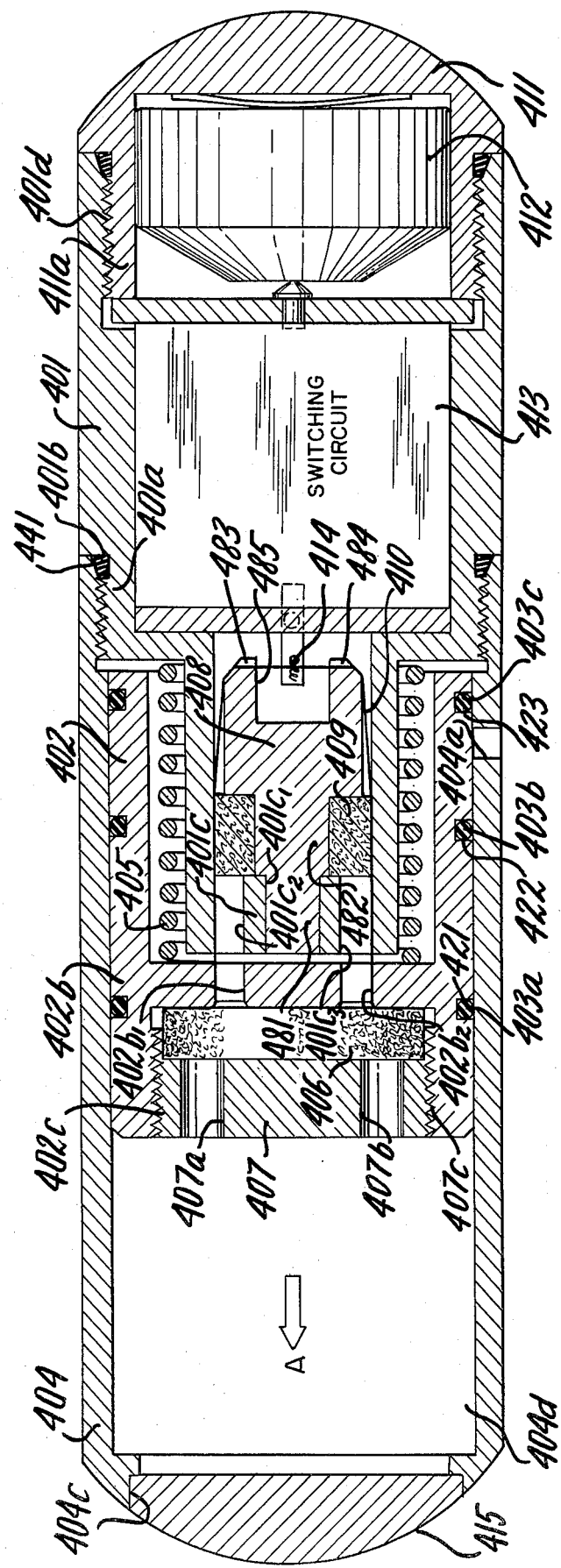
FIG. 4 is a cross-sectional view of another embodiment of capsule for medical use and having of drug-releasing means instead of the collecting means thereof shown in FIG. 1.
Figure 5:
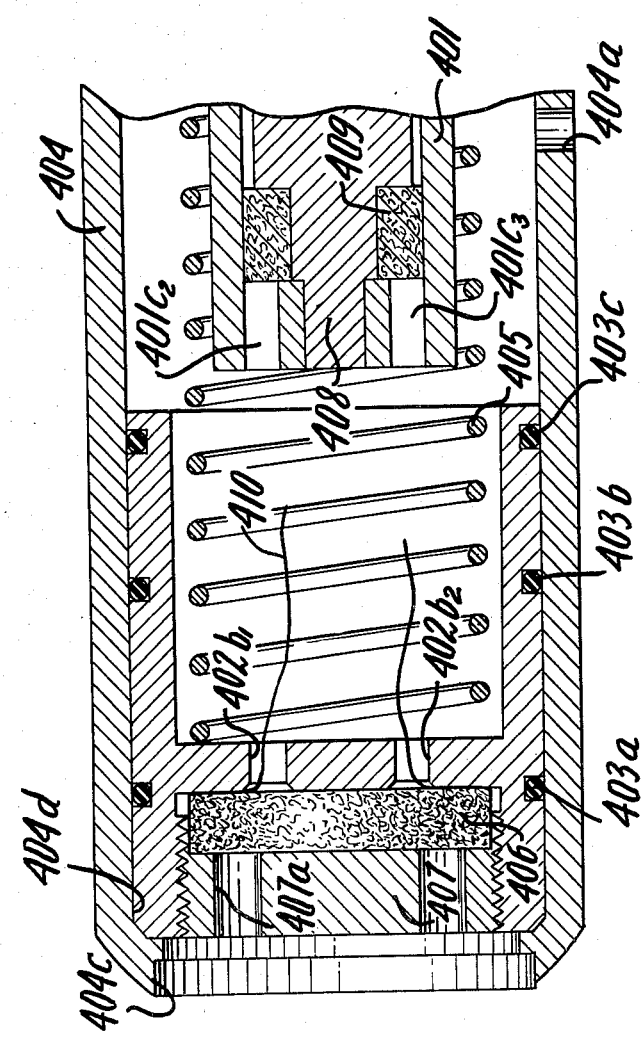
FIG. 5 is a fragmentary cross-sectional view of the capsule shown in FIG. 4 but showing the parts in a different operating state.

This example 2 pertains to a capsule for medical use to release drugs and will be described referring to FIG. 4 and FIG. 5.

"401" is a cylindrical body frame constituted of stepped portions "401a" and an inlaid groove "401b" along the circumference thereof, a supporting portion "401c" having inserting holes "401c1, 401c2 & 401c3" at the front end portion thereof and an inserting groove "401d" at the internal circumference of the rear end thereof. "402" is a releasing cylinder set up in a supporting portion "402b" having inserting holes "402b1 & 402b2" at the intermediate portion thereof and a threaded portion "402c" for fixing a thread guard "407", described later, on the front end portion thereof along the internal circumference thereof. The releasing cylinder "402" is fitted slidably with the internal circumferential surface of an external cylinder "404" through sealing packing rings "403a, 403b & 403c". And on the external circumference of said releasing cylinder "402" are recessed grooves "421, 422 & 423" for receiving said sealing packing rings "403a, 403b & 403c" respectively. "404" is an external cylinder having an inserting groove "404c" at the front end portion thereof and a projected portion "441" at the rear internal circumference thereof for insertion into said inserting groove "401b" for shielding the front half portion of the body frame "401". Furthermore, an inhaling hole "404a" is located at the external circumference of the cylinder "404" near the said projected portion "441", and a sealing plug "415" for sealing drugs or the like is inserted into the inserting groove "404c" of the front end portion of the external cylinder "404". A circular coil spring "405" is compressed between said supporting portion "402b" and said stepped portion "401a" to push out drugs packed in an empty space "404d" formed in the external cylinder "404" by moving said releasing cylinder "402" in the direction of arrow mark A. A disc-shaped packing "406" is inserted in the front recessed portion of said releasing cylinder "402" and this packing "406" is fixed to the releasing cylinder "402" by the disc-shaped thread guard "407" having driving holes "407a & 407b" and a threaded portion "407c" which is screw threaded into the threaded portion "402c" of said releasing cylinder "402". "408" is a cylindrical disc-shaped thread hanger press-fitted into said inserting hole "401c1" at the front end "481"

thereof and has a stepped "482" at the external circumference thereof, cutting slits "483 & 484" to wedge a thread "410", described later, thereinto and a circular empty hole "485" at the rear end portion thereof. "409" is a circular disc-shaped packing to seal the internal side of said frame "401" and is fixed to said stepped portion "482". "410" is a flexible thread to restrain the movement of said releasing cylinder "402" in the direction of arrow mark A by the compressive pushing force of said spring "405" and one end of said thread "410" is fixed by pressure between said supporting portion "402b" and said packing "406" and wedged into the cutting slits "483 & 484" through the inserting holes "402$b_1$ & 401$c_2$" and the other end of the thread "410" is fixed in the same manner through the inserting holes "402$b_1$ & 401$c_2$". "411" is a rear cover having a projected portion "411a" inserted into said inserting groove "410d" of the internal circumference of said body frame "401" for shielding the rear end portion of said body frame "401" and for holding a power cell "412" for a switching circuit "413" and a heater "414", described later, therein. The said switching circuit "413" is mounted in the body frame "401" and flows current to said heater "414" by switching-on the heater only upon receiving an instructing electric wave signal transmitted from external of the capsule. The said heater "414" is connected to said switching circuit "413" and said power cell "412" and fixed so as to make contact with said thread "410".

Hereafter, the operation of said capsule for medical use will be described.

This capsule, wherein the desired drug is previously packed in the empty space "404d" of the external cylinder "404", is inserted in a live body by swallowing down or the like process and when it arrives at the specified place, the electric wave signal is transmitted from outside the live body and the thread "410" is cut-off by fusing with the heater "414" by means of actuating the switching circuit "413" according to current flow thereto from the power cell "412" and thereby the releasing cylinder "402" moves in the direction of arrow mark A by the biasing force of the spring "405". At this time, the sealing plug "415" is pushed out of the inserting groove "404C" by the pressure of the releasing cylinder "402" whose movement pushes the drugs packed in the empty space "404d" outside of the capsule. And at the same time, when the end point of the releasing cylinder "402" slips out from the projected portion located near the external cylinder "404", the empty space in which is held the spring "405" is prevented from becoming negative pressure by permeating body fluid thereinto. Then the releasing cylinder "402" moves till the front end surface thereof comes into contact with the front end point of the external cylinder "404" as shown in FIG. 5 thereby forcing all of the drug out perfectly from the empty space "404d" of the external cylinder "404".

This example 2 is very effective in medical treatment because it can concentrically release the drugs packed in the empty space of the external cylinder to the diseased part of digestive tract.

EXAMPLE 3

Figure 6:
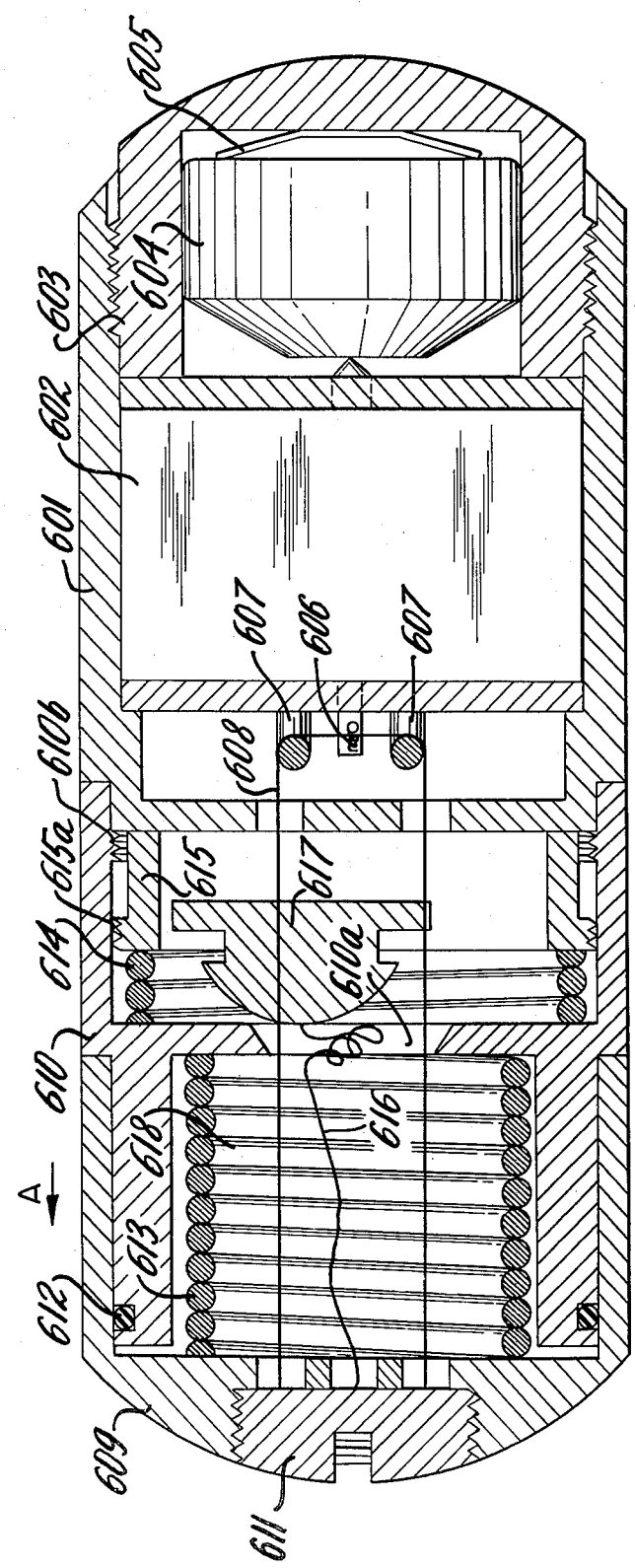
FIG. 6 is a cross-sectional view of another embodiment of the capsule of the type separated into two parts at the time of collecting the inside body samples or releasing drugs into the body.
Figure 8:
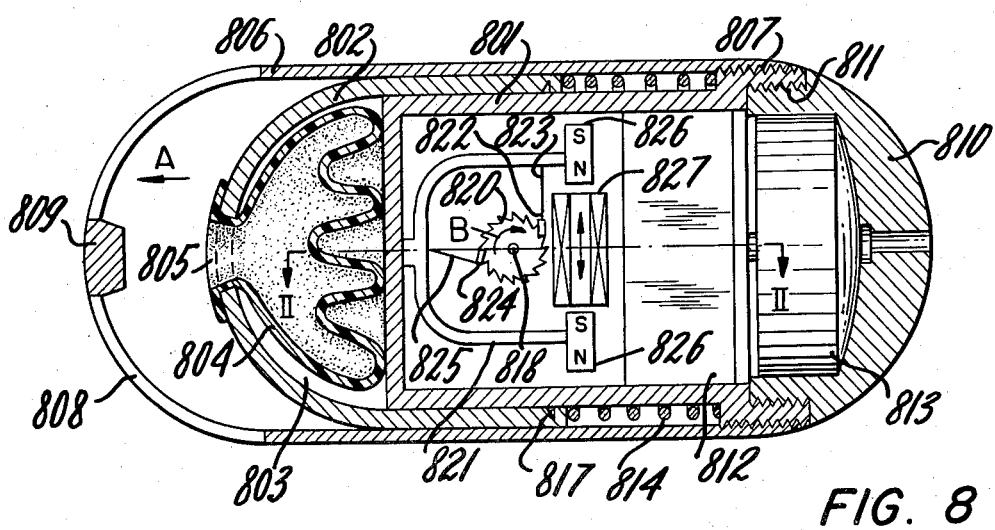
FIG. 8 is a cross-sectional view of a further embodiment of the capsule for medical use wherein an external portion of the capsule is interchangeable.

This example 3 pertains to a capsule for medical use and which can be separated into two parts at the time of either collecting the inside body sample or releasing drugs into the body and will be described referring to FIG. 6.

This embodiment is a collecting capsule having a separating mechanism which is to separate a signal receiving portion to receive an external instructing electric wave signal at operating time thereof and a sample collecting portion. The signal receiving portion for receiving the external instructing electric wave signal is composed of a cylindrical frame "601", a circuit compartment "602" having an electric circuit mounted therein, a power cell "604" connected to said electric circuit, a heater filament "606" connected to the electric circuit as an electric load thereof and thread hangers "607". On the other hand, the sample collecting portion to collect samples is composed of a recovery frame "610" having sealed-up connection to said cylindrical frame "601" by means of a light press-fit, an external cylinder "609" inserted slidably over one end of said recovering frame "610", a thread guard "611" screwed in said external cylinder "609", a compressed coil spring "613" for pushing said external cylinder "609" in to the direction of arrow mark A against said recovering frame "610" and a valve thread "616" having one end fixed on said thread guard "611" and the other end fixed on a valve "617". The separating mechanism between the two parts, that is, said signal receiving portion to receive an external electric wave instructing signal and said sample collecting portion, is composed of a pressing cylinder "615" built in the rightward portion of said recovery frame "610" (as viewed in FIG. 6) and screwed via a threaded portion "615a" completely through a threaded portion "610b" of said recovery frame "610" so that the frame "610" and cylinder "615" are disconnected from each other as shown in FIG. 6 and a separating coil spring "614" to push said pressing cylinder "615". A thread "608" connects the two parts, i.e., said signal receiving and said sample collecting portions, by the said thread guard "611" to resist against the pushing forces of said compressed coil spring "613" and said compressed separating coil spring "614". The thread guard "611" has a threaded portion to fix the said thread "608" and a valve thread "616" by screwing into said external cylinder "609". "603" is a guard frame for housing the electric cell "604", "605" is a spring for keeping good electric contact with said electric cell "604" and "612" is an O-shaped sealing ring.

Hereafter, the operation of this capsule will be described. The filament "606" is energized by the power cell "604" by the electric circuit in the circuit compartment "602" in response to receipt of an instructing electric wave signal. And then the said thread "608" is cut off by fusing due to temperature rise of the filament "606" to 260° C. to 270° C. due to electric current flow and at the same time, the said recovery frame "610" separates from the frame "601" by the pushing force of the separating coil spring "614" through the pressing cylinder "615". And simultaneously with the cutting of the thread "608", the external cylinder "609" begins to slide in the direction of the arrow mark "A" along the recovering frame "610" by the pushing force of the pressing coil spring "613" through the O-shaped sealing ring "612" mounted thereon. Just then, a space "618" between the recovery frame "610" and the external cylinder "609" undergoes a volume change and a negative pressure develops therein, so that the body fluid flows therein from a collecting hole "610a" and the valve thread "616" is gradually pulled in the direction of the arrow mark "A" by the relative slide movements of the recovery frame "610" and the external cylinder "609", and the valve "617" attached to the end thereof seals the collecting hole "610a" when the external cylinder "609" moves sufficiently from the recovery frame "610" by fitting into said collecting hole "610a".

As described above, as this example is constructed such that the portion to collect samples or release drugs and the portion in which are packed the electric circuit and power cell can be separated, it is possible that the costly parts such as the electric circuit and power cell can be repeatedly used following a simple disinfect operation.

EXAMPLE 4

Figure 7:
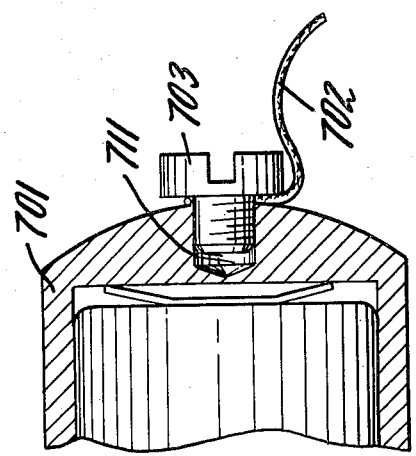
FIG. 7 is a cross-sectional view of another embodiment of the capsule for medical use whereto a thread is attached to the capsule end so that it can be pulled out from the mouth after collecting the inside body samples or releasing the drugs.

This example 4 pertains to a capsule for medical use and in which a thread is fixed thereon so as to pull up said capsule from the body's mouth after collecting samples or releasing drugs and will be described referring to FIG. 7.

The construction of this capsule is to fix a supporting thread "702" to a body frame "701" with a flat-headed machine screw "703" screwed into a female threaded blind hole "711" drilled in the said body frame "701".

As mentioned above, the capsules described in the examples 1 to 3 are recovered in the feces together with the digesting material, but this kind of capsule in this example takes hardly any time due to easy pull-up in the case of collecting samples or releasing drugs at places near the mouth such as stomach, duodenum, etc., accordingly the medical results can be obtained without delay.

EXAMPLE 5

This example 5 relates to a capsule for collecting inside body samples for medical use wherein the external circumference portion thereof is exchangeable and will be described referring to FIGS. 8 to 11.

"801" is an end-closed cylindrical body frame and "802" is an external cylinder and slidable on the frame "801" and defining therebetween an empty space "803" formed between the front wall of said body frame "801" and said external cylinder "802" so as to undergo a volume change as described later. "804" is a flexible receiving bag made of soft material and is placed in said empty space "803" and the end portion thereof is mounted attachably and detachably on a hole "805" formed on the end center of said external cylinder "802".

"806" is a cylindrical cover protecting the body frame "801" and the external cylinder "802" by covering almost their entire exteriors and this cover "806" is fixed to a threaded portion of the rear end external circumference of the body frame "801", so this screwing fix is detachable. A plurality of slits or holes or net-construction are formed in the front end portion of said cover "806" to thereby form an open wall "808", and a plug "809" corresponding with the hole "805" of the external cylinder "802" is set at the center portion of the open wall "808" as a one-body construction. "810" is a rear cover mounted detachably on a threaded portion "811" of the rear end internal circumference of the body frame "801" and shielding the rear end portion thereof and also comprising therein a power cell "813" for a circuit block "812" (described later) mounted in the body frame "801".

Figure 9:
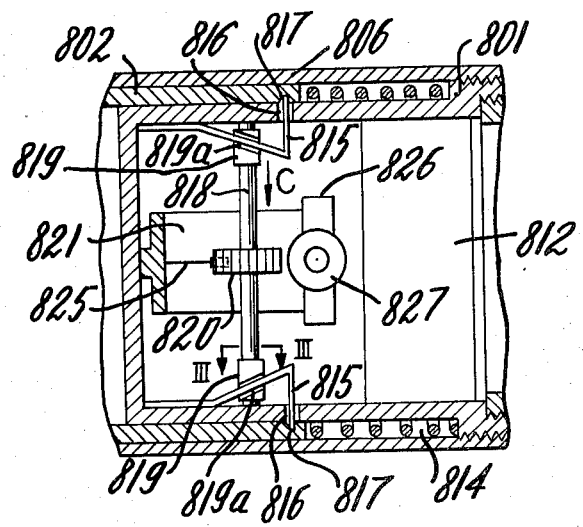
FIG. 9 is a partial sectional view along the line II—II of FIG. 8.

"814" is a spring loaded between the rear edge of external cylinder "802" and the rear stepped portion of body frame "801" and this spring "814" is compressed so that the extensible force thereof is in the direction of arrow mark A causing the external cylinder "802" to seperate from the body frame "801". "815 & 815", as shown in FIG. 9, are a pair of stoppers for arresting said spring "814" under compressed condition and are made of sheet springs. And these stoppers "815 & 815" are set in the inside of body frame "801" and the end points thereof are pushed out to the external circumference of body frame "801" through holes "816 & 816" located so as to make alignment with corresponding arresting slots "817 & 817" formed on the internal circumference of external cylinder "802".

Figure 10:
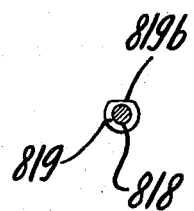
FIG. 10 is a partial sectional view along the line III—III of FIG. 9.

"818" is a cam shaft mounted rotatably in the body frame "801" and at both ends of this cam shaft "818" are fixed cams "819 & 819" for undoing each said stopper "815" from its corresponding slot "817" and a rachet wheel "820" is secured at the center portion of the cam shaft "818". A pair of spiral cam slots "819a & 819a" are formed on the circumference of said cams "819 & 819" and these slots engage with some portions of the stoppers "815 & 815" so that if the cam shaft "818" rotates in the direction of arrow mark "B", the end points of the stoppers are drawn inwardly in to the direction of arrow mark "C". A cut-off portion "819b" to formed on the circumference of each of the cams "819 & 819" as shown in FIG. 10, and when the stoppers coincide with these cut-off portions "819b & 819b" (called reset condition), the end points thereof protrude by the spring force themselves in the direction of arrow mark C.

"821" is a tuning fork mounted in the body frame "801" and a feeding claw "822" is mounted on the one side of the free ends of said tuning fork "821" through a supporting spring "823" and a holding claw "824" is mounted on the base-side of tuning fork "821" through a supporting spring "825". "826 & 826" are magnets rigidly fixed on the respective free ends of the tuning fork "812" and a coil "827", used for both receiving and driving, supported with the circuit block "812" is arranged between said magnets "826 & 826".

Upon supplying an AC electric wave signal having a certain specified frequency to said coil "827", the tuning fork "801" together with the magnets "826 & 826" vibrates with a resonant frequency of said wave signal according to the AC magnetic field produced from said coil "827". Thereby, the feeding claw "822" is given vibrations having sufficient strokes and the said ratchet "820" is constructed to make the cam shaft "818" rotate in a stepwise manner in the direction of arrow mark "B" a pitch one by one under the control of the holding claw "824".

Figure 11:
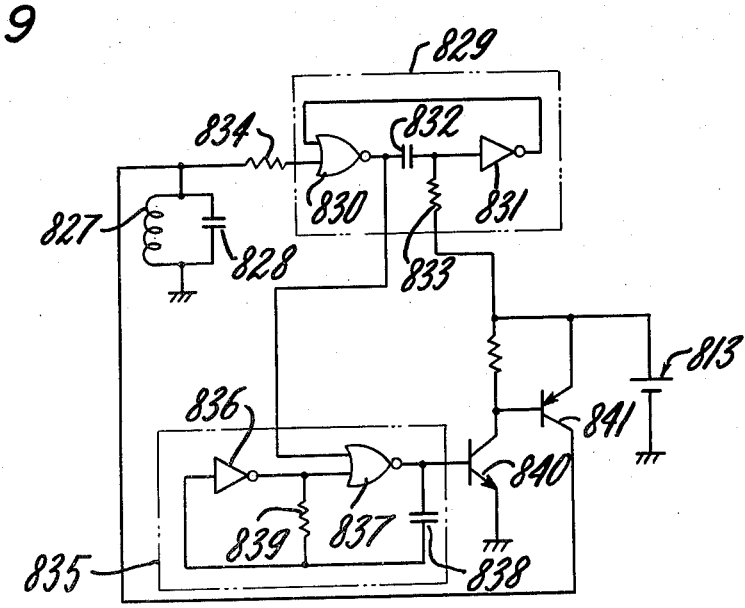
FIG. 11 is an electric schematic of one embodiment of receiving and driving circuit for the capsule shown in FIG. 8.

FIG. 11 shows one example of receiving and driving circuit and "813 & 827" are respectively said cell and said coil and also other elements are contained in the said circuit block "812". The coil "827" with a condenser "828" forms a parallel resonance circuit and produces resonance according to the reception of the instructing electric wave signal of frequency similar to the tuning fork resonant frequency. "829" is a monostable multivibrator composed of a NOR gate "830", an inverter "831", a condenser "832" and a resistor "833" and when the input of said NOR gate "830" through a protective resistor "834" goes over the threshold voltage thereof as the said parallel resonance circuit produces resonance, this monostable multivibrator "829" is triggered, and from just this time the output of said NOR gate "830" becomes "LOW" only during the given period of time that the voltage change occurred by the condenser "832" and the resistor "833" goes over the threshold voltage of the NOR gate "830".

"835" is a clock circuit constituted of an astable multivibrator composed of an inverter "836", a NOR gate "837", a condenser "838" and a resistor "839", and the oscillating frequency of this clock circuit "835" is previously tuned to the resonant frequency of the tuning fork "821" fixed with the magnets "826 & 826". The clock circuit "835" is in action only when the signal supplied from said NOR gate "830" to the NOR gate "837" becomes "LOW". Furthermore, the oscillating signal of said clock circuit "835" is amplified by a driving circuit composed of transistors "840 & 841" and charged to the coil "827" and thereby the oscillating signal makes the tuning fork "821" vibrate.

Hereafter, the operation of the capsule for medical use and constructed as described above will be described. As shown in the figures under the condition to arrest the external cylinder "802" to the stopper "815" of the body frame "801", this capsule is inserted in a live body by swallowing down or the like method. And when the capsule arrives at the desired place to collect samples, such as the intenstines, or the like, the instructing electromagnetic wave signal having the definite frequency is transmitted from external of the body.

Whereupon, by the reception of this instructing electromagnetic wave signal, the resonant circuit composed of the coil "827" and the condenser "828" begins to resonate and thereby the monostable multivibrator is triggered and the clock circuit "835" is in action according to the output thereof only during the given period of time. That is to say, the coil "827" is charged by the definite frequency signal and the tuning fork "821" vibrates with the feeding claw "822" and thereby the ratchet "820" is fed a pitch one by one whereby the cam shaft "818" is incrementally rotated in the direction of arrow mark B. Whereupon, the stoppers "815 & 815" are drawn inwardly in the direction of arrow mark C by the cams "819 & 819" and the end points thereof are slipped out from the arresting slots "817 & 817", so that the external cylinder "802" moves in the direction of arrow mark A by the force of the spring "814" and finally the hole "805" of the external cylinder "802" is sealed up by the plug "809". In the moving process of this external cylinder "802", the volume of the empty space "803" is sharply expanded so that the samples (such as the contents in the intestines) are absorbed in the receiving bag "804" mounted in the empty space "803". And the samples in the receiving bag "804" are sealed up with the plug "809" and are taken out with the capsule in that condition from the anus.

The pulse width of said monostable multivibrator "829", that is, the time period of the oscillating time of the said tuning fork "821", is set to the time it takes to make the said ratchet "820" rotate one revolution, so that thereby the cams "819 & 819", are to stop the resetting position thereof. Accordingly, after taking out the capsule from inside the body and removing the cover "806" and the external cylinder from the body frame "801" and then removing the receiving bag "804" which has the samples therein together with the external cylinder "802", then a new external cylinder "802" fixed to a new receiving bag "804" and the new cover "806" are again mounted on the body frame "801" whereby the capsule can be reused and repeatedly used in this fashion. After some repeated use thereof, the power cell "813" should be exchanged.

As described above, the portions which directly contact with the body fluid or the like, such as the external cover "806" and the rear cover "810", are changeable on the body frame "801" which contains the driving mechanism of the capsule such as the circuit block "812", the coil "827", the tuning fork "821", the ratchet "820", the stopper "815", etc. so that with repeated use of the capsule, the deterging trouble can be saved and also the patient's hygienical aversions can be allayed and further this kind of capsule for medical use can be put to practical use by this example because of its easy handling and economical improvement.

Furthermore, it goes without saying that the mounting construction of the said cover and the rear cover for the body frame are not limited to the screwing in method as shown in the figures, and other well known types of detachable connectors can be used. And this example can be applied to the capsule to release drugs into the body by using the reduction of the said empty space, to push out the drugs.

While a few embodiments (examples 1 to 5 ) of the invention have been illustrated and described in detail, it is particularly understood that the invention is not limited thereto or thereby. For example, as the driving mechanism, there can be used built-in type solenoids, a cylinder type mechanisms utilizing heat expansion of fluid by a built-in heater, a or driving mechanisms using an AC magnetic field applied from external of the body.

What is claimed is:

1. A capsule for medical use comprising: a cylindrical body frame having a cylindrical stepped portion; an external cylinder mounted on an end portion of said cylindrical body frame and having at least one through hole extending through a wall portion thereof; a recovery cylinder mounted for sliding movement from one position to another position within said external cylinder and having at least one through hole extending through a wall portion thereof and capable of communicating with said through hole of said external cylinder during sliding movement of said recovery cylinder in said external cylinder; biasing means for exerting a biasing force on said recovery cylinder tending to slidably move the same along said external cylinder from said one position to said another position; actuatable retaining means for releasably retaining said recovery cylinder at said one position within said external cylinder against said biasing force and operative when actuated for releasing said recovery cylinder whereby said biasing force effects sliding movement of said recovery cylinder to said another position; an electric switching circuit including receiving means for switching on the switching circuit when an externally transmitted instructing electric signal is received by said receiving means to actuate said retaining means to thereby release said recovery cylinder; and means for supplying electric power to said switching circuit to enable operation of said switching circuit; said recovery cylinder including two axially spaced chambers one of which surrounds said cylindrical stepped portion of said cylindrical body frame when said recovery cylinder is in said one position, and means for hermetically separating said one of said two chambers from the other and being disposed within said other of said two chambers; said retaining means comprising a thread hanger removably fixed and inserted into said cylindrical stepped portion of said body frame, and a thread coacting with said thread hanger for retaining said recovery cylinder at said one position against said biasing force, said thread extending over said thread hanger and having its ends secured in place by said means for hermetically separating said one of said two chambers from the other and being tensioned by said biasing means; said receiving means including a heating device for heat-cutting said thread in response to the instructing electric signal thereby releasing said recovery cylinder whereby said biasing means effects sliding movement of said recovery cylinder to said another position and during such sliding movement a sample to be collected flows through the communicating through holes of said recovery cylinder and said external cylinder into the empty space formed behind the moving recovery cylinder.

2. The capsule for medical use according to claim 1; wherein said means for hermetically separating said two chambers comprises a pillar-shaped plug inserted into a damper hole provided at a front portion of said external cylinder and through which the air in the chamber defined by the interior surface of said external cylinder is discharged.

3. A capsule for medical use comprising: a cylindrical body frame; an external cylinder mounted on an end portion of said cylindrical body frame and having at least one through hole extending through a wall portion thereof; a recovery cylinder mounted for sliding movement from one position to another position within said external cylinder and having at least one through hole extending through a wall portion thereof and capable of communicating with said through hole of said external cylinder during sliding movement of said recovery cylinder in said external cylinder; biasing means for exerting a biasing force on said recovery cylinder tending to slidably move the same along said external cylinder from said one position to said another position; actuatable retaining means for releasably retaining said recovery cylinder at said one position within said external cylinder against said biasing force and operative when actuated for releasing said recovery cylinder whereby said biasing force effects sliding movement of said recovery cylinder to said another position; an electric switching circuit including receiving means for switching on the switching circuit when an externally transmitted instructing electric signal is received by said receiving means to actuate said retaining means to thereby release said recovery cylinder; means for supplying electric power to said switching circuit to enable operation of said switching circuit; a drug packed in the empty space defined in the internal portion of said external cylinder; and a sealing plug for closing said through hole of said external cylinder.

4. The capsule for medical use according to claim 3; wherein said recovery cylinder includes two chambers one of which surrounds said cylindrical stepped portion of said cylindrical body frame, and means for hermetically separating said one of said two chambers from the other and being disposed within said other of said two chambers; said retaining means comprising a thread hanger removably fixed and inserted into said cylindrical stepped portion of said body frame, and a thread coacting with said thread hanger for retaining said recovery cylinder at said one position against said biasing force, said thread extending over said thread hanger and having its ends secured in place by said means for hermetically separating said one of said two chambers from the other and being tensioned by said biasing means; said receiving means including a heating device for heat-cutting the thread in response to the instructing electric signal thereby releasing said recovery cylinder whereby said biasing means effects sliding movement of said recovery cylinder to said another position and during such sliding movement the drug discharges through the through hole of said external cylinder.

5. A capsule for medical use comprising: a cylindrical body frame; an external cylinder mounted on an end portion of said cylindrical body frame and having at least one through hole extending through a wall portion thereof; a recovery cylinder mounted for sliding movement from one position to another position within said external cylinder and having at least one through hole extending through a wall portion thereof and capable of communicating with said through hole of said external cylinder during sliding movement of said recovery cylinder in said external cylinder; biasing means for exerting a biasing force on said recovery cylinder tending to slidably move the same along said external cylinder from said one position to said another position; actuatable retaining means for releasably retaining said recovery cylinder at said one position within said external cylinder against said biasing force and operative when actuated for releasing said recovery cylinder whereby said biasing force effects sliding movement of said recovery cylinder to said another position; an electric switching circuit including receiving means for switching on the switching circuit when an externally transmitted instructing electric signal is received by said receiving means to actuate said retaining means to thereby release said recovery cylinder; means for supplying electric power to said switching circuit to enable operation of said switching circuit; and wherein said recovery cylinder includes a flexible receiving bag made of a soft material detachably mounted in the space defined by the interior of said recovery cylinder and having a hole disposed in communication with said through hole of said recovery cylinder whereby a sample can be collected through the through hole of said external cylinder and said hole of said flexible receiving bag during sliding movement of said recovery cylinder toward said another position.

6. The capsule for medical use according to claim 3, wherein said switching circuit includes a circuit block having means for receiving the instructing electric signal, a tuning fork mounted within said cylindrical body frame and operated by the signal generated from said circuit block and having attached thereto a feeding claw, and a cam shaft rotatably mounted within said body frame and having mounted thereon a cam and a ratchet wheel which is in engagement with said feeding claw; and wherein said retaining means includes a stopper having one end portion mounted on the inside of said body frame and the other end portion in engagement with the internal surface of said recovery cylinder through a hole formed in said body frame and which is in contact with said cam on said cam shaft whereby said other end portion of said stopper is disengaged from said recovery cylinder by said cam when said tuning fork is operated by the signal generated from said circuit block to thereby release said recovery cylinder for sliding movement.

7. A capsule for use in discharging drugs into or collecting samples from a live body comprising: an elongate hollow housing; a movable member mounted within said housing for sliding movement therealong from an initial position to a final position and dividing the interior of said housing into a drug storage space at the forward side of said movable member and a sample collecting space at the rearward side of said movable member; means for communicating at least one of said drug storage and sample collecting spaces to the exterior of said housing; biasing means for exerting a biasing force on said movable member biasing said movable member toward its final position; actuatable retaining means for releasably retaining said movable member in its initial position against the biasing force exerted by said biasing means and operative when actuated for releasing said movable member; and electric circuit means including a tuner circuit responsive to an externally transmitted signal of a predetermined frequency for effecting actuation of said retaining means thereby releasing said movable member to undergo sliding movement toward said final position by said biasing means; whereby drugs stored in said drug storage space can be pushed out of said housing into the live body ahead of the sliding movable member or samples from the live body can be withdrawn into said housing in said sample collecting space behind the sliding movable member.

8. A capsule according to claim 7; wherein said means for communicating comprises means for communicating said sample collecting space to the exterior of said housing only during the course of sliding movement of said movable member.

9. A capsule according to claim 7; wherein said retaining means includes a meltable thread secured to said movable member and strong enough to retain said movable member in said initial position against the biasing force exerted by said biasing means; and wherein said electric circuit means includes a heater energized in response to receipt of said signal of predetermined frequency to melt said thread thereby actuating said retaining means to release said movable member.

* * * * *